(12) United States Patent
Flowers et al.

(10) Patent No.: US 7,196,223 B2
(45) Date of Patent: Mar. 27, 2007

(54) HIGHER ALCOHOLS FOR SOLVENTS IN AMINE PRODUCTION

(75) Inventors: Tom L. Flowers, Pale, FL (US); Anthony K. Uriarte, Pensacola, FL (US); Shannon Davis, Cantonment, FL (US); Gregory J. Ward, Katy, TX (US)

(73) Assignee: Solutia, Inc., St. Louis, MO (US)

( * ) Notice: Subject to any disclaimer, the term of this patent is extended or adjusted under 35 U.S.C. 154(b) by 9 days.

(21) Appl. No.: 11/119,790

(22) Filed: May 3, 2005

(65) Prior Publication Data

US 2006/0252965 A1 Nov. 9, 2006

(51) Int. Cl.
*C07C 209/48* (2006.01)
(52) U.S. Cl. ............... 564/415; 564/490; 564/491; 564/492; 564/493
(58) Field of Classification Search ............... None
See application file for complete search history.

(56) References Cited

U.S. PATENT DOCUMENTS

| | | | |
|---|---|---|---|
| 3,821,305 A | | 6/1974 | Bartalini |
| 4,375,003 A | * | 2/1983 | Allain et al. ............... 564/492 |
| 4,429,159 A | | 1/1984 | Cutchens |
| 5,886,227 A | * | 3/1999 | Vedage et al. ............. 564/490 |
| 6,281,388 B1 | | 8/2001 | Goodwin, III |
| 6,469,211 B2 | | 10/2002 | Ansmann |
| 2004/0181093 A1 | * | 9/2004 | Kim et al. ................. 564/415 |

* cited by examiner

*Primary Examiner*—Brian Davis
(74) *Attorney, Agent, or Firm*—Jones, Tullar & Cooper, P.C.

(57) ABSTRACT

A nitrile-containing mixture, which includes a nitrile dissolved in a higher alcohol solvent, and hydrogen are fed to a reactor containing a catalyst. An amine is produced by hydrogenating the nitrile that is dissolved in the higher alcohol solvent. In a preferred embodiment, the reactor also contains a caustic solution. The preferred nitrile-containing mixture includes octadecanedinitrile (ODDN) and hexanol to produce a preferred octadecanediamine (ODDA) through hydrogenation.

21 Claims, No Drawings

HIGHER ALCOHOLS FOR SOLVENTS IN AMINE PRODUCTION

BACKGROUND OF INVENTION

1. Field of the Invention

The present invention relates to a process for hydrogenating nitrites to primary amines over a sponge metal catalyst. The nitrile is dissolved in a higher alcohol solvent prior to hydrogenation.

2. Description of Related Art

It is well known that amines may be produced by the catalytic hydrogenation of nitrites in the presence of catalysts and other substances such as a caustic solution and/or a solvent. Normally, the solvents used in hydrogenation of nitrites to amines are low molecular weight alcohols, amides, or ethers such as methanol, ethanol, dimethylacetamide, or dioxane. However, these prior solvents are all flammable which is particularly hazardous when mixed with a pyrophoric catalyst such as a sponge nickel catalyst. Furthermore, the use of highly volatile materials such as ethanol is especially hazardous since quick evaporation of the solvent promotes ignition of the catalyst. To prevent ignition, the solvent-catalyst mixture must be handled in an environment free of oxygen.

BRIEF SUMMARY OF THE INVENTION

The present invention is directed to a process for hydrogenating a nitrile to an amine by first preparing a nitrile-containing mixture including the nitrile dissolved in a higher alcohol solvent, preferably n-hexanol. "Higher alcohol solvents" is defined herein to include alcohols having a higher molecular weight than ethanol and methanol. Preferably, the higher alcohol solvents include, but are not limited to, C-5 to C-12 alcohols, diols, triols, and aromatic alcohols. These higher alcohol solvents are generally non-volatile and non-flammable. For example, n-hexanol has a flash point above 140° F. and it does not exhibit any unusual safety or health problems.

Some amine and nitrile compounds are solid at normal room temperature, for example, octadecanediamine (ODDA) and octadecanedinitrile (ODDN). ODDN has a melting point of 65–70° C. Therefore, a solvent is needed to handle these materials in standard low pressure nitrile hydrogenation technology. Since the C-18 dinitrile (ODDN) and C-18 diamine (ODDA) are waxy amorphous solids, non-polar paraffin type solvents are quite good solvents for this material. In addition, water is at least sparingly soluble in some higher alcohol solvents, such as n-hexanol, and this is important in order to monitor and control the water concentration in the process. By using a higher alcohol solvent that is non-volatile and non-flammable, the hazards of handling the solvent-catalyst mixture are greatly reduced.

DETAILED DESCRIPTION OF THE INVENTION

A continuous hydrogenation process that converts nitrites to amines in a liquid phase over a suspended, sponge metal catalyst is carried out by first preparing a nitrile-containing mixture by dissolving a nitrile in a higher alcohol solvent. "Higher alcohol solvents" is defined herein to include alcohols having a higher molecular weight than ethanol and methanol. Preferred higher alcohol solvents include, but are not limited to, C-5 to C-12 alcohols, diols, triols, and aromatic alcohols. In one preferred embodiment, the higher alcohol solvent is n-hexanol. The preferred catalyst is a sponge-type metal catalyst, most preferably a sponge nickel catalyst including iron and chromium added to promote the hydrogenation reaction. Most preferably, the sponge nickel catalyst contains about 85% nickel, 10% aluminum, 2% chromium and 2% iron. Additionally, sponge cobalt catalysts may be used. The hydrogenation is preferably carried out in the presence of a caustic solution. A preferred caustic solution includes 25 wt. % caustic material in water. The caustic material preferably comprises an alkali metal hydroxide. More preferably, the caustic material is a blend of two or more alkali metal hydroxides. For example, the caustic material is preferably a blend containing 50 wt. % sodium hydroxide and 50 wt. % potassium hydroxide.

In a preferred process for the production of an amine, such as octadecanediamine, in high yield and selectivity, the process may be carried out at pressures of 45–150 psig and at temperatures of 70° to 100° C., by feeding hydrogen and the nitrile-containing mixture into a liquid reaction medium containing, along with the amine produced, water, caustic solution and a finely divided nickel catalyst dispersed in the liquid components of the reaction medium. The catalyst, which preferably is sponge-type nickel catalyst, with or without promoter metals such as chromium and/or iron, loses some of its activity during hydrogenation.

To maintain a given level of catalytic activity within the catalytic mass, it is necessary for the catalyst in the reaction medium to be gradually regenerated preferably as described by Cutchens, et al. in U.S. Pat. No. 4,429,159, which is incorporated herein by reference. This regeneration is effected by discharging a quantity of reaction medium which contains catalyst into the regeneration vessel, allowing the catalyst to settle, decanting the organic upper layer back to the reaction vessel, and washing the catalyst with water to remove contaminants from the catalyst before it is recycled to the reactor. The recycled catalyst may consist of a mixture of fresh catalyst and of recycled catalyst if addition of a small amount of fresh catalyst is required to increase the catalyst activity in the reactor.

In order to increase the effectiveness of the low pressure nitrile hydrogenation process of the present invention, an effective amount of an inexpensive caustic hydroxide is preferably incorporated in the sponge nickel catalyst to enhance the selectivity of the reaction. The hydroxide is preferably a hydroxide of a Group IA ("alkali metal") element of the periodic table, selected from the group consisting of lithium, sodium, potassium, rubidium, cesium, and mixtures thereof. More preferably, the caustic alkali metal hydroxide is sodium hydroxide, potassium hydroxide, cesium hydroxide, and mixtures thereof.

The catalyst suitable for use in the present invention is a sponge type catalyst, also known as "skeletal" or "Raney®-type" metal catalysts. The preferred nickel catalyst used in the low-pressure hydrogenation process of the present invention is sponge nickel. The catalyst is commercially available from a number of sources (W.R. Grace and Co.; Degussa; Johnson Matthey), or it may be manufactured using any number of methods described in the literature, for instance by Mozingo in Organic Syntheses Collected Volume 3, p. 181; and Fieser and Fieser, Reagents for Organic Synthesis, Vol. 1, pp. 723–731 and references cited therein.

The catalyst is preferably prepared by first obtaining the proper weight of catalyst in water, and then washing it free of water with dioxane followed by washing with the higher alcohol solvent, for example, n-hexanol.

According to the present invention, a wide variety of nitrites can be hydrogenated to give the corresponding amines. The hydrogenation procedure is based on a routine method for hydrogenation of adiponitrile (ADN) to hexamethylenediamine (HMD). For example, the chemical reaction of octadecanedinitrile (ODDN) to octadecanediamine (ODDA) using a sponge nickel catalyst is depicted below:

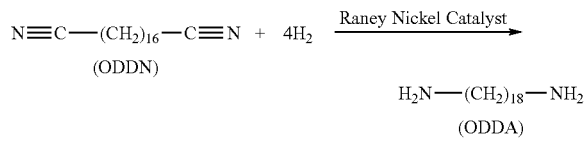

The primary modification to this hydrogenation procedure is the use of a higher alcohol solvent, preferably n-hexanol, with the nitrile.

The present invention is applicable to the process for the production of any amine including aliphatic and aromatic amines and their derivatives, such as octadecanediamine, hexamethylenediamine, benzylamine, tallow amines, etc., produced from a nitrile including aliphatic and aromatic nitriles and their derivatives such as octadecanedinitrile, tallow nitrites, benzyl nitrites, etc., in which a catalyst is suspended in a liquid reaction medium.

The hydrogenation is carried out using a suspended catalyst. Suitable reactors for hydrogenation in the suspension mode are stirred vessels, jet loop reactors or bubble columns. In a preferred embodiment, the hydrogenation is carried out at a pressure of 50–500 psig, most preferably 100–500 psig, and at temperatures of 75–150° C., most preferably 90–110° C., by feeding hydrogen and a nitrile-containing mixture into a liquid reaction medium.

EXAMPLE

The following example illustrates the use of n-hexanol as the higher alcohol solvent for the hydrogenation of ODDN to ODDA. It should become apparent to one skilled in the art that similar benefits arise from the use of other nitriles, amines, and higher alcohol solvents. The present invention is not limited by the following sample.

A one-liter autoclave reactor equipped with double turbine blades, Dispersimax™-type agitator, a coil extending to the bottom to circulate a heat transfer fluid from a temperature controlled bath for temperature control, and a hydrogen feed line fitted with a stainless steel frit positioned below the liquid level is used to react hydrogen with octadecanedinitrile. Hydrogen is fed from a cylinder equipped with a pressure gauge and a regulator to add hydrogen to the reactor when the pressure drops. The hydrogen flows through a mass flow meter. A 50% by weight nitrile-containing mixture of octadecanedinitrile in n-hexanol, is pumped to the autoclave with an Isco Model 500D syringe pump. To the autoclave is charged 37.5 grams of sponge nickel catalyst with iron and chromium added to promote the hydrogenation reaction. The sponge nickel catalyst most preferably contains about 85% nickel, 10% aluminum, 2% chromium and 2% iron. The catalyst is washed with water three times, three times with dioxane, and three times with n-hexanol. The washed catalyst and n-hexanol slurry amounting to 50 ml is charged to the autoclave. Also, 265 ml of n-hexanol and 3 ml of 25 wt. % caustic solution in water are charged. In this example, the 25 wt. % caustic is a blend containing 50 wt. % sodium hydroxide and 50 wt. % potassium hydroxide. The agitator is turned on, the autoclave heated to 60° C., purged three times with nitrogen, purged three times with hydrogen, and then pressured to 500 psig with hydrogen. The autoclave is then heated to 90° C., pressure checked for 5 minutes. The feed of the nitrile-containing mixture containing 0.04 wt. % water is then started to the autoclave at 5 ml per minute using the syringe pump. Pressure is maintained at 500 psig and temperature at 90° C. during the run. After 27 minutes, the feed is stopped, a 150-gram sample is withdrawn from the autoclave, and then the feed is restarted at the same conditions. This procedure is then repeated for a total of six cycles. Assay of the product material (excluding the solvent) from the sixth cycle is 90% octadecanediamine produced from octadecanedinitrile that was assayed at 91% by area count normalization.

Three runs were completed with n-hexanol as the solvent to compare the effect of a caustic solution and a change in pressure using a similar procedure as indicated above with exceptions as provided. The first run used 50% ODDN in n-hexanol as the feed at a feed rate of 5 ml/min and no caustic solution was added to the autoclave. The temperature was 90° C. and the pressure was 500 psig. This no-caustic run was terminated after two cycles due to very long hydrogen half lives. Therefore, while the caustic solution does not appear to play a critical role with respect to selectivity for this process, it does play an important role in preventing catalyst deactivation. The second run was identical to the initial example with the inclusion of 3 ml of caustic solution. This run performed well with no signs of catalyst deactivation, and good selectivity. The final run was identical to the second run with the exception that it was conducted at 100 psig. The low-pressure run appeared to have performed well. No signs of catalyst deactivation occurred. However, inspection of the chromatogram shows the levels of certain impurities were higher in this low-pressure run, and it is possible that some of the nitrile was not completely converted. Therefore, it is preferred to conduct the conversion at a higher pressure to ensure good overall conversion of the nitrile.

COMPARATIVE EXAMPLES

Dioxane is known to be compatible with low pressure nitrile hydrogenation technologies, but it does present some signification ES&H problems for scale up. Dioxane is flammable and it is a suspected carcinogen. Therefore, different solvents were selected and tested to determine the extent to which the solvent would dissolve ODDA.

The solvent selection process involved identifying a variety of different types of solvents and testing the extent to which the material would dissolve ODDA. The basis for comparison was dioxane, so 0.25 g of dried, solvent free ODDA was weighed into a sample vial and 0.75 g of solvent was added. The vial was then placed into an oven at 60° C., and the extent to which the diamine would dissolve was observed visually. The solvents evaluated were sulfolane, 1-methyl-2-pyrrolidinone, propylene carbonate, 2-methoxyethyl ether, and n-hexanol. This testing was qualitative in nature, and no solubility limits were measured. However, it was observed that n-hexanol was the best solvent, 2-methoxyethyl ether was a fair solvent (similar 1,4-dioxane), and the others were poor solvents. Therefore, it appears the ODDA is more paraffin-like than it is amine-like since the least polar solvents appear to work the best. In fact, n-hexanol is such a good solvent, that the concentration of the amine in solvent can be raised to 50 wt. % while still handling the reaction product as a liquid at 50° C. In addition, n-hexanol has a flash point of 145° F. and the following safety ratings:

Health Rating: 1—Slight
Flammability Rating: 2—Moderate
Reactivity Rating: 1—Slight
Contact Rating: 2—Moderate Therefore, the crude material is much easier to handle from an environmental, safety and hygiene point of view, and the fact that the solution concentration can be doubled means the material can be processed more quickly at lower cost.

Although the present invention has been disclosed in terms of a preferred embodiment, it will be understood that numerous additional modifications and variations could be made thereto without departing from the scope of the invention as defined by the following claims.

We claim:

1. A method for the production of an amine from a nitrile by hydrogenation comprising,
   a) feeding hydrogen and a nitrile-containing mixture into a reactor having a sponge metal catalyst, said nitrile-containing mixture includes a nitrile dissolved in a higher alcohol solvent; and
   b) hydrogenating said nitrile to form an amine.

2. The method of claim 1, wherein said reactor further includes a caustic solution including a caustic material.

3. The method of claim 2, wherein said caustic material is an alkali metal hydroxide.

4. The method of claim 2, wherein said caustic solution includes 25 wt. % of a caustic material in water.

5. The method of claim 4, wherein the caustic material is a blend containing 50 wt. % sodium hydroxide and 50 wt. % potassium hydroxide.

6. The method of claim 1, wherein said higher alcohol solvent is selected from the group consisting of C-5 to C-12 alcohols, diols, triols and aromatic alcohols.

7. The method of claim 6, wherein said higher alcohol solvent is n-hexanol.

8. The method of claim 7, wherein said nitrile is octadecanedinitrile.

9. The method of claim 1, wherein said nitrile is selected from the group consisting of aliphatic nitriles, aromatic nitriles and their derivatives.

10. The method of claim 9, wherein said nitrile is selected from the group consisting of proprionitrile, tallow nitriles and benzyl nitriles.

11. The method of claim 9, wherein said nitrile is octadecanedinitrile.

12. The method of claim 9, wherein said higher alcohol solvent is n-hexanol.

13. The method of claim 1, wherein said amine is selected from the group consisting of aliphatic amines, aromatic amines, and their derivatives.

14. The method of claim 13, wherein said amine is selected from the group consisting of hexamethylene diamine, benzyl amine, and tallow amines.

15. The method of claim 13, wherein said amine is octadecanediamine.

16. The method of claim 1, wherein said sponge metal catalyst is a sponge-type nickel catalyst.

17. The process of claim 1, wherein said reactor is operated at a temperature of 75–150° C.

18. The process of claim 17, wherein said reactor is operated at a temperature of 90–110° C.

19. The process of claim 1, wherein said reactor is operated at a pressure of 50–500 psig.

20. The process of claim 19, wherein said reactor is operated at a pressure of 100–500 psig.

21. The process of claim 1, wherein said nitrile-containing mixture includes 50 wt. % of said nitrile and 50 wt. % of said higher alcohol solvent.

* * * * *